US012582516B2

(12) United States Patent
Attia et al.

(10) Patent No.: US 12,582,516 B2
(45) Date of Patent: Mar. 24, 2026

(54) MULTIFOCAL INTRAOCULAR LENS

(71) Applicant: HANITA LENSES LTD., Kibbutz Hanita (IL)

(72) Inventors: Mickael Attia, Rehovot (IL); Alexander Brodsky, Petah Tikva (IL); Natan Kaplan, Lod (IL); Israel Grossinger, Karmei Yossef (IL)

(73) Assignee: HANITA LENSES LTD. (IL)

( * ) Notice: Subject to any disclaimer, the term of this patent is extended or adjusted under 35 U.S.C. 154(b) by 820 days.

(21) Appl. No.: 17/276,198

(22) PCT Filed: Sep. 12, 2019

(86) PCT No.: PCT/IL2019/051025
§ 371 (c)(1),
(2) Date: Mar. 15, 2021

(87) PCT Pub. No.: WO2020/053864
PCT Pub. Date: Mar. 19, 2020

(65) Prior Publication Data
US 2022/0031447 A1      Feb. 3, 2022

Related U.S. Application Data

(60) Provisional application No. 62/730,769, filed on Sep. 13, 2018.

(51) Int. Cl.
*A61F 2/16* (2006.01)
*G02B 5/18* (2006.01)
(52) U.S. Cl.
CPC .......... *A61F 2/1618* (2013.01); *A61F 2/1656* (2013.01); *G02B 5/1876* (2013.01)

(58) Field of Classification Search
CPC ............................ A61F 2/1618; A61F 2/1656
See application file for complete search history.

(56) References Cited

U.S. PATENT DOCUMENTS

| | | | |
|---|---|---|---|
| 4,637,697 A | 1/1987 | Freeman | |
| 5,344,447 A | 9/1994 | Swanson | |
| | | (Continued) | |

FOREIGN PATENT DOCUMENTS

| | | |
|---|---|---|
| CN | 108135691 | 6/2018 |
| JP | 2009503622 | 1/2009 |
| | (Continued) | |

OTHER PUBLICATIONS

Osipov Vladimir et al., "Application of nanoimprinting technique for fabrication of trifocal diffractive lens with sine-like radial profile", Journal of Biomedical Optics, SPIE, vol. 20, No. 2, Feb. 1, 2015, p. 25008.

(Continued)

*Primary Examiner* — Jerrah Edwards
*Assistant Examiner* — Aren Patel
(74) *Attorney, Agent, or Firm* — ISUS INTELLECTUAL PROPERTY PLLC; Anthony Jason Mirabito

(57) ABSTRACT

A multifocal IOL including at least one diffractive surface including a plurality of discrete, adjacent, diffractive, concentric rings, having a radial phase profile cross-section with a near-symmetrical diffractive surface topography, and an odd number, greater than three, of diffractive orders and an asymmetrical distribution of energy flux over the diffractive orders.

13 Claims, 6 Drawing Sheets

(56) References Cited

U.S. PATENT DOCUMENTS

| | | | |
|---|---|---|---|
| 5,699,142 A | 12/1997 | Lee et al. | |
| 5,760,871 A | 6/1998 | Kosoburd et al. | |
| 6,536,899 B1 | 3/2003 | Fiala | |
| 8,240,850 B2 | 8/2012 | Apter et al. | |
| 8,747,466 B2 | 6/2014 | Weeber et al. | |
| 9,223,148 B2 | 12/2015 | Fiala et al. | |
| 9,335,564 B2 | 5/2016 | Choi et al. | |
| 11,000,365 B2 | 5/2021 | Choi et al. | |
| 11,556,018 B2 | 1/2023 | Holmström et al. | |
| 2006/0098163 A1 | 5/2006 | Bandhauer et al. | |
| 2007/0032866 A1 | 2/2007 | Portney | |
| 2007/0182921 A1 | 8/2007 | Zhang et al. | |
| 2009/0122262 A1* | 5/2009 | Hong | A61F 2/1618 623/6.3 |
| 2009/0187242 A1* | 7/2009 | Weeber | A61F 2/1654 623/6.24 |
| 2009/0240328 A1 | 9/2009 | Treushnikov et al. | |
| 2009/0268155 A1 | 10/2009 | Weeber | |
| 2010/0321635 A1 | 12/2010 | Apter et al. | |
| 2011/0267693 A1 | 11/2011 | Kobayashi et al. | |
| 2011/0270390 A1* | 11/2011 | Kobayashi | A61F 2/1618 623/6.38 |
| 2012/0283825 A1 | 11/2012 | Houbrechts et al. | |
| 2015/0190224 A1* | 7/2015 | Sieber | A61F 2/1656 623/6.22 |
| 2015/0250583 A1 | 9/2015 | Rosen et al. | |
| 2016/0220352 A1 | 8/2016 | Choi et al. | |
| 2016/0228238 A1* | 8/2016 | Risser | G02C 7/022 |
| 2017/0209259 A1* | 7/2017 | Choi | G02B 5/1876 |
| 2019/0049752 A1* | 2/2019 | Van Heugten | G02B 3/08 |

FOREIGN PATENT DOCUMENTS

| | | | |
|---|---|---|---|
| JP | 2009526275 | | 7/2009 |
| JP | 2015217292 | | 12/2015 |
| WO | 9411765 | | 5/1994 |
| WO | 2009027438 | A2 | 3/2009 |
| WO | 2010079537 | | 7/2010 |
| WO | 2012078763 | A1 | 6/2012 |
| WO | 2017055503 | | 4/2017 |
| WO | 2017136310 | | 8/2017 |
| WO | 2019020435 | A1 | 1/2019 |

OTHER PUBLICATIONS

Search Report—corresponding European Application No. 23180491, dated Oct. 6, 2023, 18 pages.

Search Report—corresponding European Application No. 23172225, dated Oct. 5, 2023, 18 pages.

Search Report—corresponding European Application No. 23180490, dated Oct. 10, 2023, 12 pages.

Wikipedia contributors. (Dec. 7, 2021). Gerchberg-Saxton algorithm. Wikipedia. Retrieved Mar. 14, 2022, from https://en.wikipedia.org/wiki/Gerchberg%E2%80%93Saxton_algorithm.

O'Shea, D. C., & SPIE. (2004). Diffractive optics: Design, fabrication, and test. Bellingham, Wash. <1000 20th St. Bellingham WA 98225-6705 USA: SPIE.

HOLO OR the Experts in Diffractive and Micro-Optics. (n.d.). HOLO OR. Retrieved Mar. 14, 2022, from http://holoor.co.il/Diffractive_optics_Applications/Application-Notes-Multifocal-Lens.htm.

Lenkova G A: "Features of optical surfaces of multifocal diffractive-refractive eye lenses", Optoelectronics, Instrumentation and Data Processing, Pleiades Publishing, Moscow, vol. 53, No. 5, Dec. 16, 2017 (Dec. 16, 2017), pp. 431-441, XP036629198.

Gori F et al: "Analytical derivation of 1-14 the optimum triplicator", Optics Communications, Elsevier, Amsterdam, NL, vol. 157, No. 1-6, Dec. 1, 1998 (Dec. 1, 1998), pp. 13-16, XP004150691.

PCT International Search Report for International Application No. PCT/IL2019/051025, mailed Jan. 21, 2020, 8pp.

PCT Written Opinion for International Application No. PCT/IL2019/051025, mailed Jan. 21, 2020, 4pp.

R. W. Gerchberg and W. O. Saxton, "A Practical Algorithm for the Determination of Phase from Image and Diffraction Plane Pictures", Optik, vol. 35 (No. 2), 237-246 (1972).

Osipov, Vladimir et al., "Application of Nanoimprinting Technique for Fabrication of Trifocal Diffractive Lens with Sine-Like Radial Profile", Journal of Biomedical Optics, 20(2), Feb. 2015, 025008, 1-7.

Office Action—Corresponding Japanese Application No. 2023-077733, dated Feb. 27, 2024, 4 pages.

* cited by examiner

MULTIFOCAL INTRAOCULAR LENS

CROSS REFERENCE TO RELATED APPLICATIONS

This application is a National Phase of PCT Patent Application No. PCT/IL2019/051025 having International filing date of Sep. 12, 2019, which claims the benefit of priority to U.S. Provisional Patent Application No. 62/730,769 filed Sep. 13, 2018, entitled "MULTIFOCAL INTRAOCULAR LENS" the contents of which are incorporated herein by reference in their entirety.

FIELD OF THE INVENTION

The present invention, in some embodiments thereof, relates to multiple focus intraocular lenses in general and, more particularly, but not exclusively to multi-focal, diffractive, intraocular ophthalmic lenses.

BACKGROUND

An intraocular lens (IOL) is a lens implanted in the eye as part of a treatment for cataracts or myopia. The multifocal intraocular lenses (IOLs) available are often able to restore visual function and allow eyeglasses independence after their implantation with great levels of patient satisfaction.

Multifocal IOLs correct far-vision, near-sightedness and all mid-range distances. Multifocal IOLs improve near vision by dividing light in different focuses, which changes the vision physiology because of the light dispersion that happens when it enters into the eye. Modern multifocal IOLs provide a more physiological division of light and, in this way, optimize the eyeglasses independence and also provide better vision quality and less visual symptoms for the patient.

The foregoing examples of the related art and limitations related therewith are intended to be illustrative and not exclusive. Other limitations of the related art will become apparent to those of skill in the art upon a reading of the specification and a study of the figures.

SUMMARY

The following embodiments and aspects thereof are described and illustrated in conjunction with systems, tools and methods which are meant to be exemplary and illustrative, not limiting in scope.

There is provided, in accordance with some embodiments of the invention, a multifocal IOL including at least one diffractive surface including a plurality of discrete, adjacent, diffractive, concentric rings, having a radial phase profile cross-section with a near-symmetrical diffractive surface topography, and an odd number, greater than three, of diffractive orders. In some embodiments, the IOL includes an asymmetrical distribution of energy flux over the diffractive orders.

In some embodiments, the IOL includes five diffractive orders. In some embodiments, the diffractive surface includes diffractive steps designed to maintain the diffractive profile unchanged in between the steps, and wherein the diffractive steps are partially inside and partially outside the base curvature of the IOL.

In some embodiments, the diffractive, concentric rings include a repetitive pattern of diffractive profiles. In some embodiments, the profiles are asymmetrical.

In some embodiments, the diffractive rings include a repetitive pattern of a single diffractive profile. In some embodiments, the diffractive rings include a repetitive pattern of two different diffractive profiles, and wherein the diffractive rings include a single transition from a first zone having a repetitive pattern of one diffractive profile to a second peripheral zone having a repetitive pattern of a second diffractive profile.

In some embodiments, height of the diffractive surface topography of the second peripheral zone is maintained constant when advancing radially outwards in respect to the center height of the IOL. In some embodiments, the radial phase profile cross-section has an asymmetrical double-peaked geometry.

In some embodiments, thickness of the IOL is variable and the curvature is maintained. In some embodiments, thickness of the IOL is variable and the curvature is variable.

In addition to the exemplary aspects and embodiments described above, further aspects and embodiments will become apparent by reference to the figures and by study of the following detailed description.

BRIEF DESCRIPTION OF THE FIGURES

Exemplary embodiments are illustrated in referenced figures. Dimensions of components and features shown in the figures are generally chosen for convenience and clarity of presentation and are not necessarily shown to scale. The figures are listed below.

DETAILED DESCRIPTION

For purposes of better understanding some embodiments of the present invention, as illustrated in FIGS. 1A to 6 of the drawings, reference is first made to the construction and operation of a multifocal intraocular lens (IOL).

Multifocal Intraocular lenses (IOL) are designed such that to produce one, two, three or more diffractive orders or foci on the optical axis such that each image focal point is formed on the retina when an object associated with the image is located at a corresponding distance from the eye. Most of the intraocular lenses are designed to have a refractive (lens) focal point and energy flux (power) that corresponds to far vision i.e. the spherical/aspherical surfaces of the lens are designed to focus an image of an object on the retina when the object is located at the far-sighted distance from the eye (>5-6 meters). The diffractive surfaces in most bifocal and trifocal lenses create additional foci at the near (30-40 cm) and intermediate distances (60-80 cm).

Most refractive-diffractive IOLs have the same general structure—a lens comprising multiple rings, each ring having a diffractive profile that is scaled to the ring width. The diffractive profiles are repeated along the radius for each Fresnel zone. In some cases, the rings are also scaled vertically (apodization).

According to an aspect of the invention there is provided an IOL comprising diffractive steps which are partially inside and partially outside the base curvature of the IOL. In some embodiments, the thickness of the IOL is variable and the curvature is constant. In some embodiments, change in curvature is produced by optimization of the sphericity between steps.

According to an aspect of some embodiments of the present invention there is provided an IOL that has a spherical surface and an aspherical surface. In some embodiments, the IOL comprises an asymmetrical number of active diffractive orders along the optical axis of the eye. In some embodiments, the IOL comprises more than three diffractive orders on the optical axis of the eye. In some embodiments, the IOL comprises five diffractive orders on the optical axis.

In some embodiments, the IOL comprises a diffractive pattern on one or more surfaces of the lens. In some embodiments, the diffractive pattern comprises a repetitive pattern of diffractive profiles. In some embodiments, the profiles are asymmetrical.

Figure 1A:
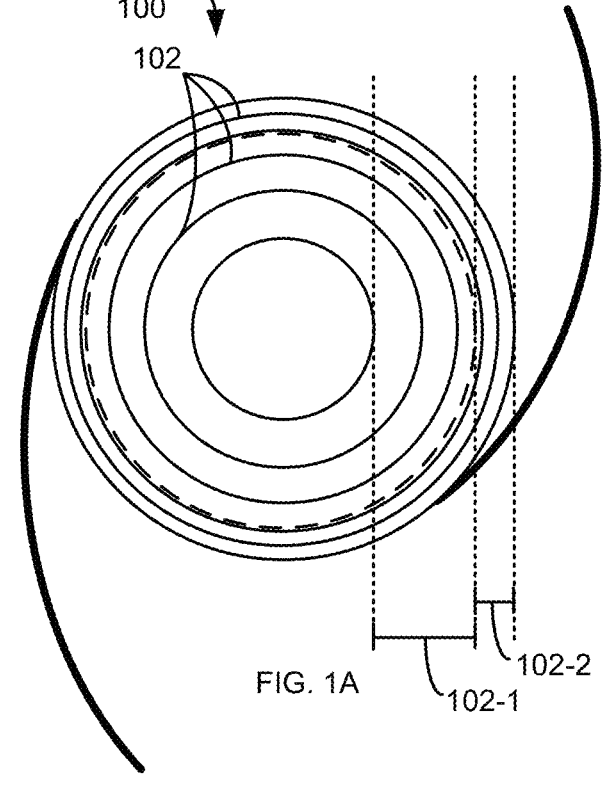
FIG. 1A is a plan view simplified illustration of a multifocal IOL.
Figure 1B:
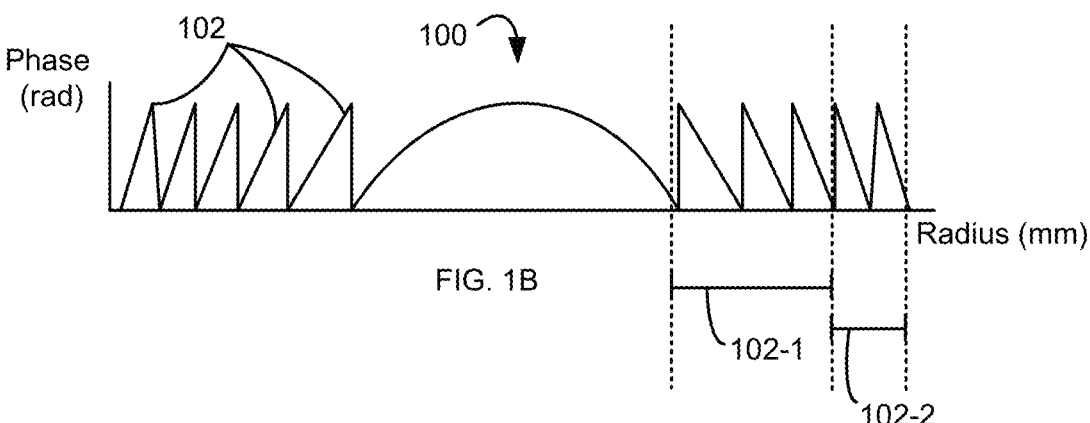
FIG. 1B is a cross-section view simplified illustration of a diffractive surface of a multifocal IOL according to some embodiments of the present invention.

Reference is now made to FIGS. 1A and 1B (not drawn to scale), in which FIG. 1A is a plan view simplified illustration of a multifocal IOL and FIG. 1B is a cross-section view simplified illustration of a diffractive surface of a multifocal IOL according to some embodiments of the present invention.

As shown in the exemplary embodiment depicted in FIG. 1A, An IOL 100 comprises a diffractive surface having a plurality of discrete, adjacent, diffractive, concentric sections or rings 102.

In some embodiments, the IOL diffractive surface comprises diffractive steps which are partially inside and partially outside the base curvature of the IOL. This induces changes in diffractive status between two steps. In some embodiments, the thickness of the IOL is variable but the curvature is maintained. In some embodiments, change in curvature is produced by optimization of the sphericity between steps.

Potential advantages in the described design are in that:
1. The designing of the diffractive steps does not change the diffractive profile in between the steps. This allows to have multifocal IOL of any added power and more efficiency for near focal lengths without losing contrast for distance.
2. Design of diffractive steps allows rays of light to be parallel to the step which is the ideal condition for diffraction.

In some embodiments, the rings are distributed along Fresnel zones (102-1/102-2). In some embodiments, and a shown in FIG. 1B, an IOL surface 150 topography features repetitive triangular forms, squared forms or parabolic forms depending on the type of lens.

Figure 2A:
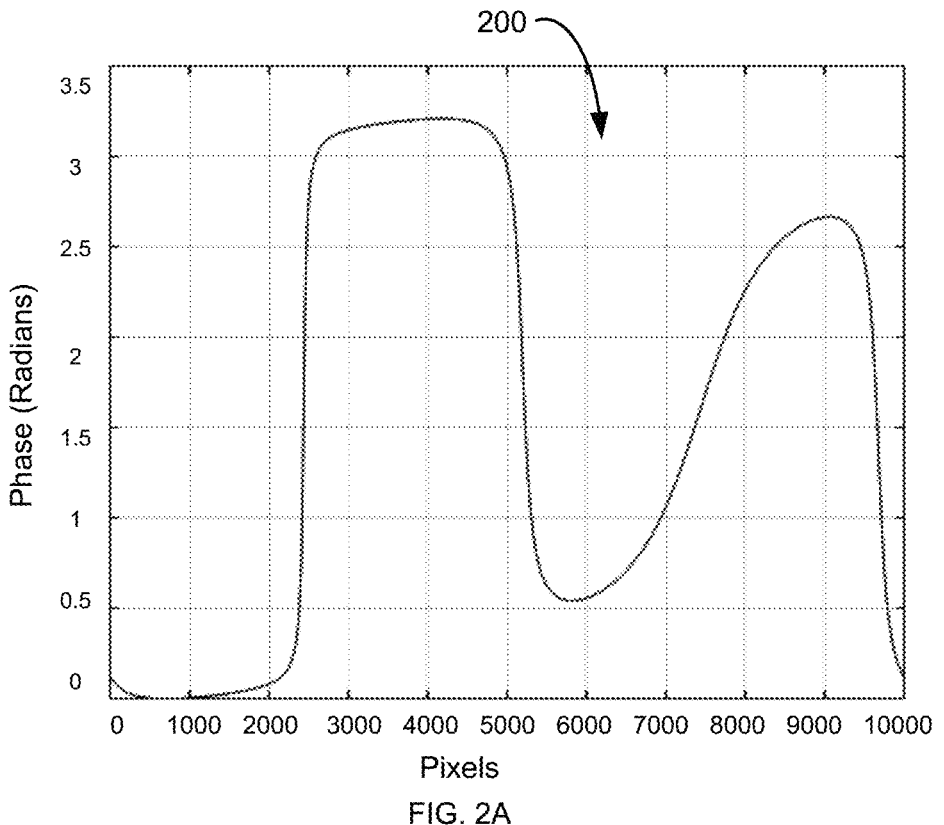
FIG. 2A is a radial, cross-section, simplified illustration of a diffractive surface topography of a portion of the IOL.
Figure 2B:
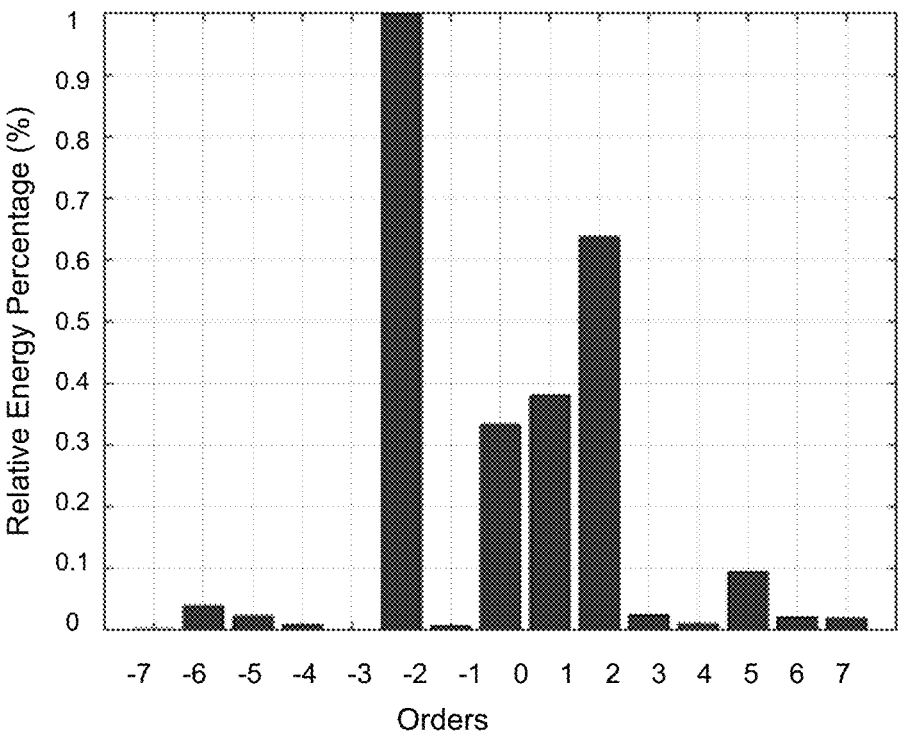
FIG. 2B is a graph of distribution of energy flux (power) levels over specific diffractive orders associated with the diffractive surface topography shown in FIG. 2A.

Reference is now made to FIG. 2A which is a radial, cross-section, simplified illustration of a diffractive surface topography of a portion of the IOL and FIG. 2B, which is a graph of distribution of energy flux (power) levels over specific diffractive orders associated with the diffractive surface topography shown in FIG. 2A.

FIG. 2A depicts a radial cross-section or radial phase profile 200 of a diffractive surface topography through a concentric ring. The specific cross-section of the radial phase profile is generated by using a Gerchberg-Saxton (GS) iterative algorithm. FIG. 2A depicts an exemplary embodiment of a radial phase profile cross-section showing an asymmetrical double-peaked cross-section having a near-symmetric local diffractive surface topography. Radial phase profile 200 is converted to a height profile which is radially and parabolically integrated to each of the Fresnel zones (rings) of the diffractive lens with a specific focal length.

The authors of this disclosure have come to learn that symmetric local diffractive surface topography function combined with an odd number of diffraction diffractive orders e.g., 1, 3, 5, 7 or 9 diffraction diffractive orders, and specifically a number of diffraction diffractive orders greater than three increase the overall light transmission efficiency of the IOL above 90% and in some cases up to at least 93%.

In some embodiments, IOL 100 comprises five diffractive orders on the optical axis. In some embodiments, one of the diffractive orders e.g., the far vision focal length has a high energy flux level. In some embodiments, one of the diffractive orders is entirely suppressed. In some embodiments, the five diffractive orders or foci correspond to the following five diffractive orders: $-2, -1, +1$ and $+2$ which are diffracted diffractive orders produced by the diffractive pattern and a single order 0 which is the refractive power produced by the spherical/aspherical surfaces of the IOL. In some embodiments, the spherical/aspherical surfaces of the lens are designed such as to focus an image on the retina when the imaged object is located at an intermediate distance from the eye, between near vision (~30-40 cm) and far vision (several meters).

In some embodiments, and as depicted in FIG. 2B, of the five diffractive orders, the diffractive order $-2$, corresponds to far vision has the highest energy flux level. In some embodiments, of the remaining diffractive orders, the diffractive order $+2$, which corresponds to near vision has the highest energy flux level. In this embodiment, the diffractive order $-1$ is suppressed.

Figure 3A:
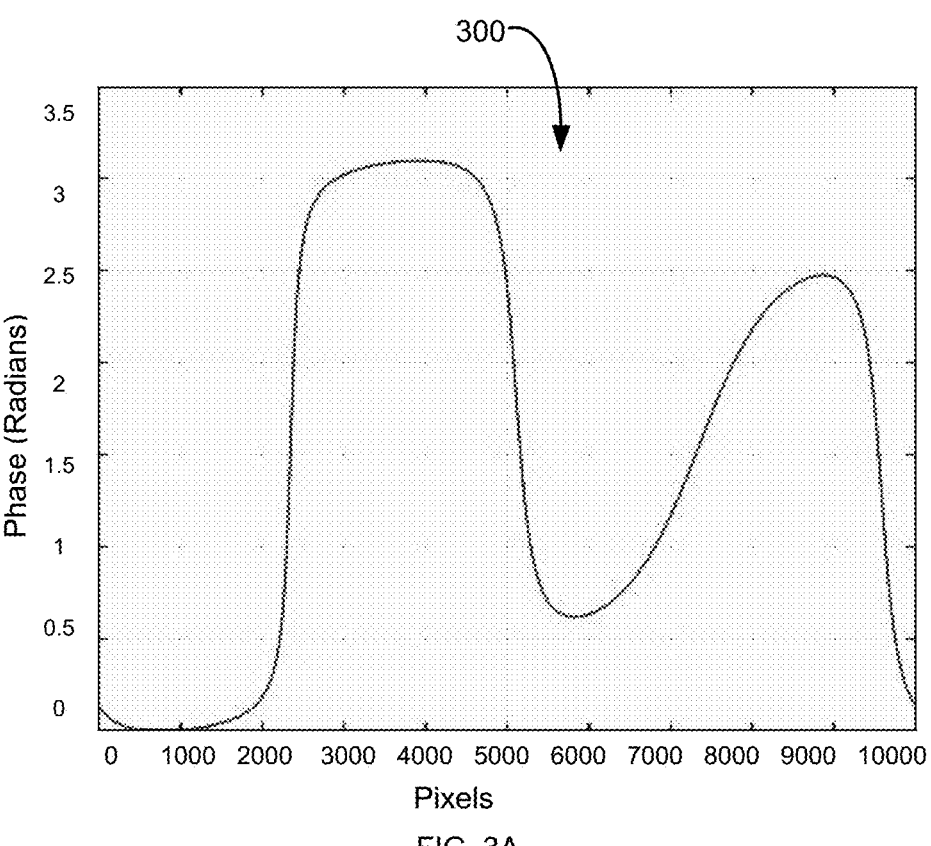
FIG. 3A is a radial, cross-section, simplified illustration of a diffractive surface topography of a portion of the IOL.
Figure 3B:
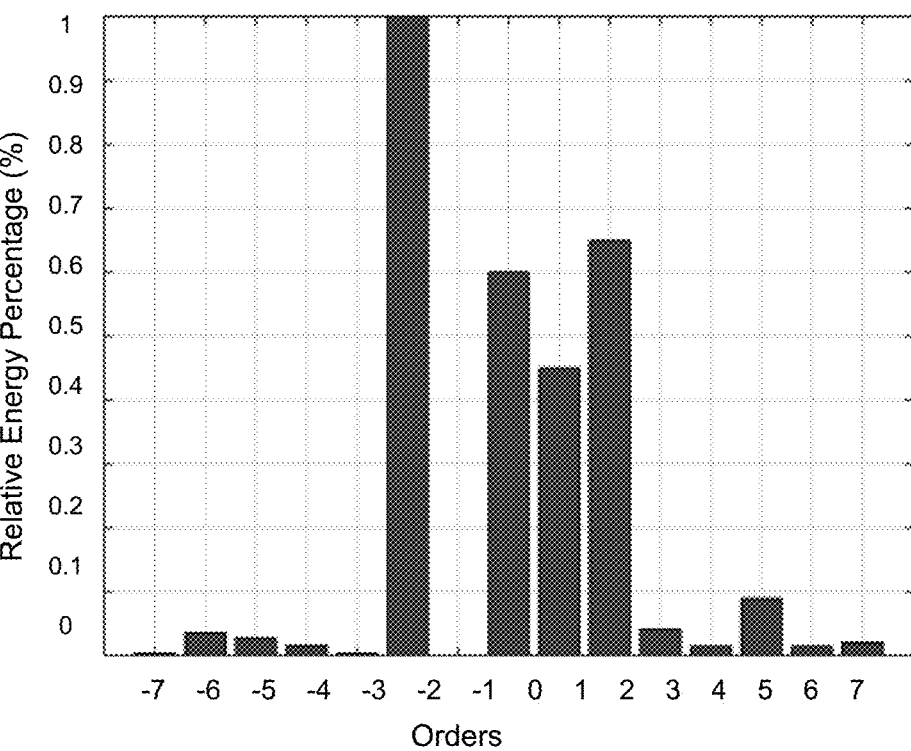
FIG. 3B is a graph of distribution of energy flux (power) levels over specific diffractive orders associated with the diffractive surface topography shown in FIG. 3A.

Reference is now made to FIG. 3A which is a radial, cross-section, simplified illustration of a diffractive surface topography of a portion of the IOL and FIG. 3B, which is a graph of energy flux levels distribution over specific diffractive orders associated with the diffractive surface topography shown in FIG. 3A.

FIGS. 3A and 3B show a design different than that illustrated in FIGS. 2A and 2B however both have been designed using the same method of profile generation by using a Gerchberg-Saxton (GS) iterative algorithm and conversion of the phase profile to a height profile which is radially and parabolically integrated to each of the Fresnel zones (rings) of the diffractive lens with a specific focal length.

FIG. 3A depicts an additional example of a radial cross-section or radial phase profile 300 of a diffractive surface topography through a concentric ring. FIG. 3A depicts an exemplary embodiment of a radial phase profile showing an asymmetrical double-peaked cross-section having a near-symmetric local diffractive surface topography. Radial phase profile 300 is converted to a height profile which is radially and parabolically integrated to each of the Fresnel zones (rings) of the diffractive lens with a specific focal length.

In some embodiments, and as depicted in FIG. 3B, of the five diffractive orders, the diffractive order −2, corresponds to far vision has the highest energy flux level. In some embodiments, of the remaining diffractive orders, the diffractive order +2, which corresponds to near vision has the highest energy flux level and the energy flux level at order 0 is higher than the energy flux level at diffractive order +1. In this embodiment, the diffractive order −1 is suppressed.

Figure 4:
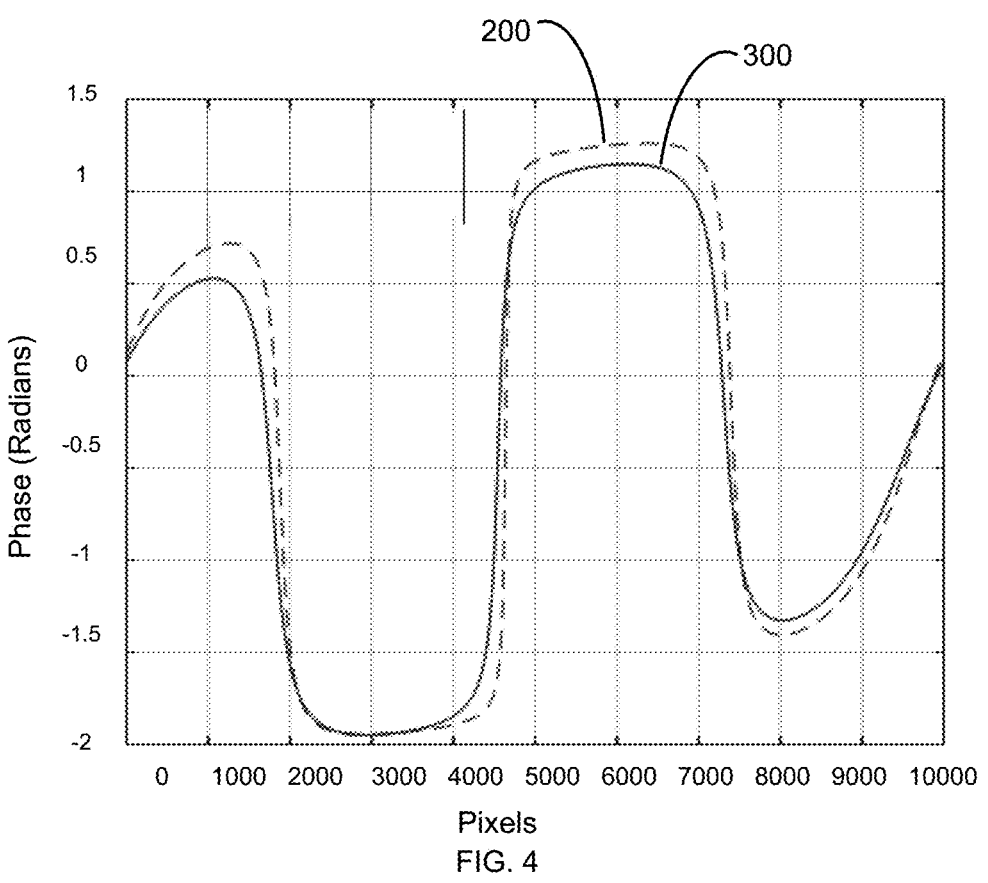
FIG. 4 is a graph superimposing two radial phase profiles in accordance with some examples of the invention.

As shown in FIG. 4, which is a graph superimposing radial phase profile 300 over radial phase profile 200 demonstrates phase differences between the designs in accordance with some examples of the invention. When using this technique with more than 5 foci (for example 7), the diffractive focal length determines the location of the far focus (diffractive order −3) and near focus (diffractive order +3) and the refractive focal length (spherical surfaces) determines the location of one of the intermediate foci (order 0). In the exemplary embodiment depicted in FIG. 4, radial phase profile 200 comprises phases: 1, 0 ,0.333, 0.38 and 0.637, wherein radial phase profile 300 comprises phases: 1, 0, 0.6, 0.45 and 0.65. In some embodiments, the IOL comprises two zones—a central zone 102-1 (FIG. 1A and FIG. 1B) and a peripheral zone 102-2. In some embodiments, the diffractive pattern of central zone 102-1 is not apodized. In some environments, the diffractive pattern of the peripheral zone 102-2 is not apodized. The height of the diffractive surface topography of zone 102-2 is maintained constant and does not have a gradual step height reduction when advancing radially outwards in respect to the center height of the IOL. This arrangement and design are planned in diffractive order to vary the intensity distribution when increasing the aperture and allow increased light flux, even if not optimally focused, with pupil dilation (low intensity environmental) light.

A potential advantage in this design is in that the apodization design allows for diffraction efficiency near 100% thus minimizing loss of light.

For modifying the intensity distribution according to the aperture size, the technique used here is to change the diffractive pattern at any radius of the intraocular lens or at one of the Fresnel Zone (or near one of them) for better performance. For this invention, the design transition occurred at radius ~1.228 mm.

Figure 5A:
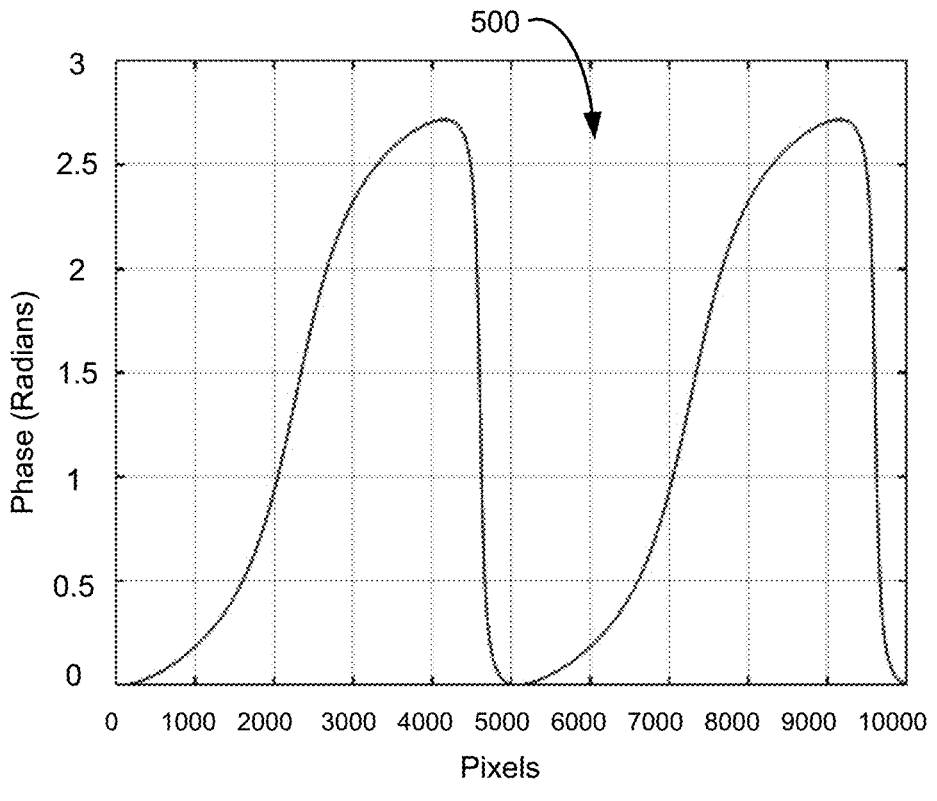
FIG. 5A is a radial, cross-section, simplified illustration of a diffractive surface topography of a portion of the IOL.
Figure 5B:
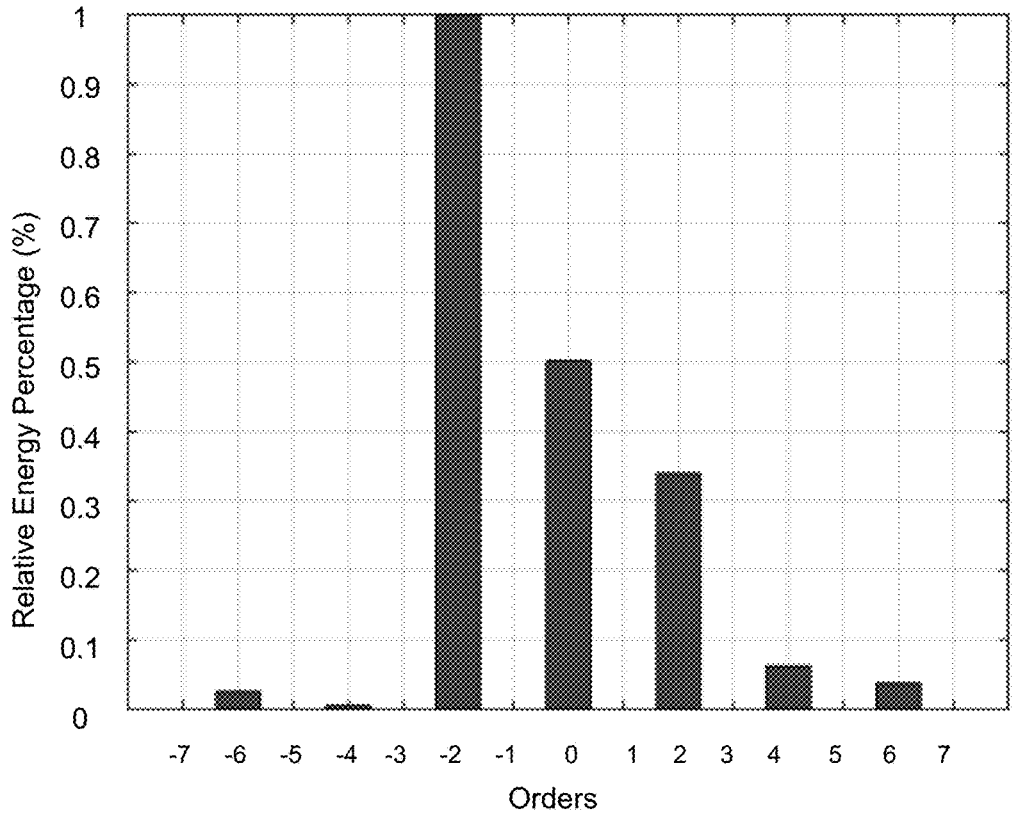
FIG. 5B is a graph of distribution of energy flux (power) levels over specific diffractive orders associated with the diffractive surface topography shown in FIG. 5A.

As shown in FIGS. 5A and 5B, in which FIG. 5A depicts an example of a radial cross-section or radial phase profile 500 of a diffractive surface topography through a concentric ring of the peripheral zone of the IOL in accordance with some embodiments of the invention. FIG. 5A depicts an exemplary embodiment of a radial phase profile cross-section at the IOL peripheral zone 102-2 showing an asymmetrical single-peaked cross-section having a near-symmetric local diffractive surface topography.

In some embodiments, a radial phase profile cross-section at the IOL peripheral zone 102-2 comprises an asymmetrical double-peaked cross-section having a near-symmetric local diffractive surface topography. Radial phase profile 500 is converted to a height profile which is radially and parabolically integrated to each of the Fresnel zones (rings) of the diffractive lens with a specific focal length.

In some embodiments, and as depicted in FIG. 5B, the flux energy level declines from the far diffractive order to the near diffractive order with two suppressed orders at −1 and +1.

The phase obtained at the source plane and used in the design (at radius >1.228 mm) depicted in FIGS. 5A and 5B is obtained using normalized target intensity [1, 0, 0.5, 0, 0.34] in the Gerchberg-Saxton (GS) algorithm.

However, in some embodiments, the other diffractive profile (after transition) can be a different diffractive design based on three or more foci and can be also a monofocal design with full energy at far vision or bifocal with energy at far vision and other foci at intermediate or near vision Also, for fine tuning of the intraocular lens, the entire diffractive height profile (before and after transition from IOL zone 102-1 to IOL zone 102-2) can be tunable. In the exemplary embodiment depicted in FIGS. 5A and 5B, the first diffractive profile before the transition has been increased by 5% and the second diffractive profile after the transition has been increased by 12%. Our multifocal IOL, based on zero order for intermediate vision, has a high efficiency—over 90%—in the used diffractive orders (−2, −1, 0, 1, 2).

Figure 6:
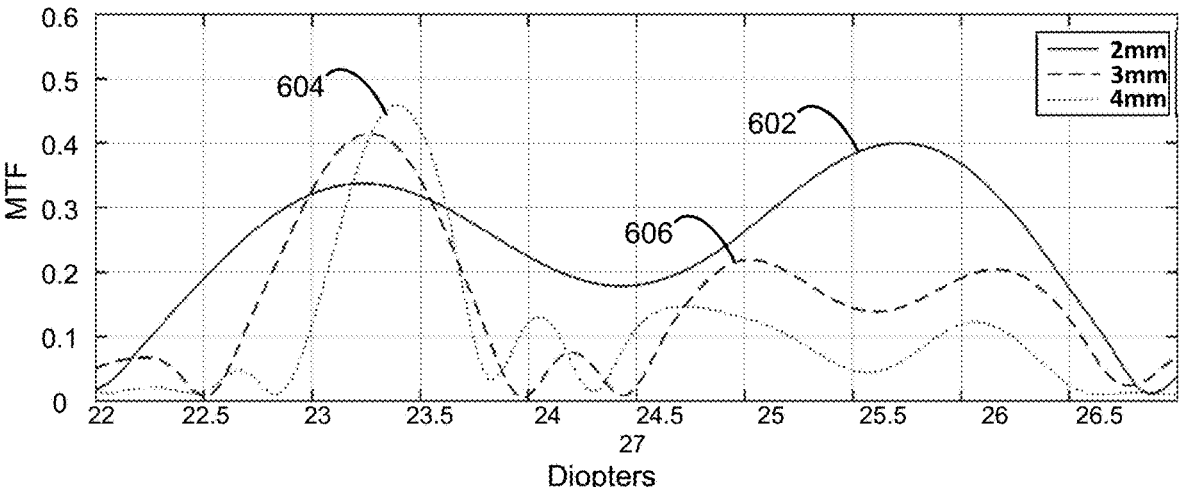
FIG. 6 is a graph of a simulation of a through-focus Modulation Transfer Function (MTF) of the IOL in accordance with some embodiments of the invention.

Reference is now made to FIG. 6, which is a graph of a simulation of a through-focus Modulation Transfer Function (MTF) of the IOL in accordance with some embodiments of the invention. As shown in the exemplary embodiment depicted in FIG. 5, three graphs are drawn for three levels of eye pupil diameter: graph 602 for a 2 mm pupil diameter (i.e., intense light condition), graph 604 for a 4.5 mm pupil diameter (i.e., low light condition) and graph 606 for a 3 mm pupil diameter (i.e., normal light condition).

The graphs depicted in FIG. 6 exhibit the biphasic nature of the IOL at all three shown levels of environmental light however, as the level of environmental light decreases changing the pupil diameter from 2 mm to 4.5 mm, the MTF value correspondingly increases on the far-sighted range of the IOL, even though it is limited from a diopter range between approximately 22 and 24.5 to a narrower diopter range between approximately 23 to 23.75 and allows for an improved low-light intensity vision.

Figure 7:
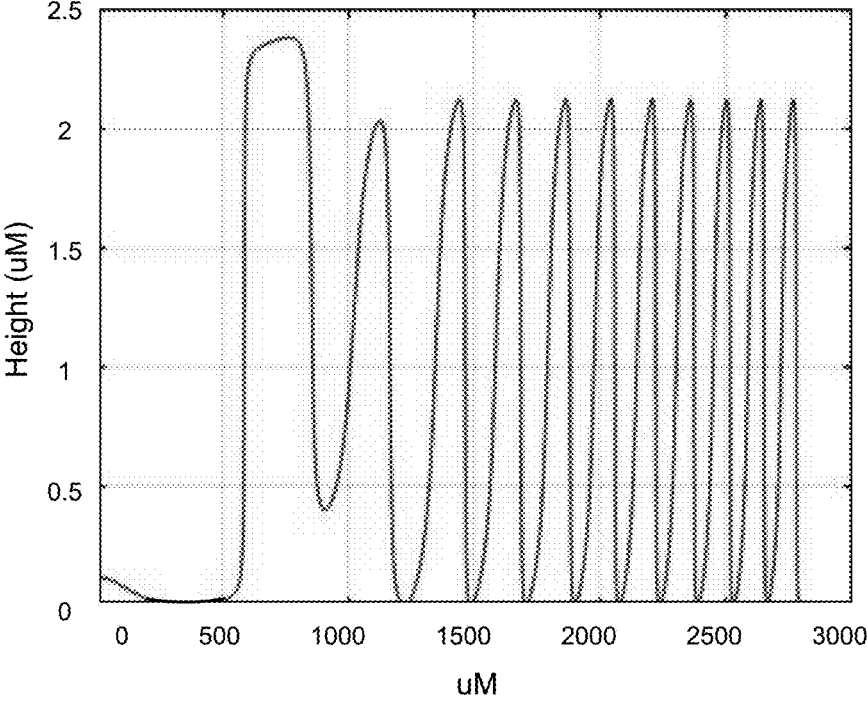
FIG. 7 is a simplified graph illustration depicting a profile of a diffractive portion of an exemplary lens in accordance with some embodiments of the current invention.

FIG. 7 which is a simplified graph illustration depicting a profile of a diffractive portion of an exemplary lens in accordance with some embodiments of the current invention. As shown in FIG. 7, the depicted cross-section profile comprises an asymmetrical single-peaked topography comprising a plurality of peaks having a height of between 1.5 and 2.5 uM dispersed along a portion of the lens radius between 0 and 3000 uM.

Throughout this application, various embodiments of this invention may be presented in a range format. It should be understood that the description in range format is merely for convenience and brevity and should not be construed as an inflexible limitation on the scope of the invention. Accordingly, the description of a range should be considered to have specifically disclosed all the possible subranges as well as individual numerical values within that range. For example, description of a range such as from 1 to 6 should be considered to have specifically disclosed subranges such as from 1 to 3, from 1 to 4, from 1 to 5, from 2 to 4, from 2 to 6, from 3 to 6 etc., as well as individual numbers within that range, for example, 1, 2, 3, 4, 5, and 6. This applies regardless of the breadth of the range.

Whenever a numerical range is indicated herein, it is meant to include any cited numeral (fractional or integral) within the indicated range. The phrases "ranging/ranges between" a first indicate number and a second indicate number and "ranging/ranges from" a first indicate number "to" a second indicate number are used herein interchangeably and are meant to include the first and second indicated numbers and all the fractional and integral numerals therebetween.

In the description and claims of the application, each of the words "comprise" "include" and "have", and forms thereof, are not necessarily limited to members in a list with which the words may be associated. In addition, where there are inconsistencies between this application and any document incorporated by reference, it is hereby intended that the present application controls.

The descriptions of the various embodiments of the present invention have been presented for purposes of illustration but are not intended to be exhaustive or limited to the embodiments disclosed. Many modifications and variations will be apparent to those of ordinary skill in the art without departing from the scope and spirit of the described embodiments. The terminology used herein was chosen to best explain the principles of the embodiments, the practical application or technical improvement over technologies found in the marketplace, or to enable others of ordinary skill in the art to understand the embodiments disclosed herein.

What is claimed is:

1. A Multifocal Intraocular Lens (IOL) comprising:

at least one diffractive surface including a plurality of discrete, adjacent, diffractive, concentric Fresnel zones, having:

a radial phase profile cross-section with a near-symmetrical local diffractive surface topography, wherein said near-symmetrical local diffractive surface topography provides a distribution of energy over five consecutive diffractive orders: −2, −1, 0, +1, and +2, and wherein said −2 order provides a far vision, said +2 order provides a near vision, said 0 order provides a first intermediate vision, and said +1 order provides a second intermediate vision, wherein said near-symmetrical local diffractive surface topography produces a diffractive pattern comprising said five consecutive orders with only said −1 order being suppressed; and wherein a combination of said near-symmetrical local diffractive surface topography and said five consecutive diffractive orders increases the overall efficiency of said IOL to more than 90% efficiency in said five consecutive diffractive orders.

2. The IOL according to claim 1, wherein said diffractive surface comprises diffractive steps designed to maintain the diffractive profile unchanged in between said steps.

3. The IOL according to claim 2, wherein said diffractive steps are partially inside and partially outside a base curvature of the IOL.

4. The IOL according to claim 1, wherein said diffractive, concentric rings comprise a repetitive pattern of diffractive profiles.

5. The IOL according to claim 4, wherein said profiles are asymmetrical.

6. The IOL according to claim 1, wherein said radial phase profile cross-section has an asymmetrical double-peaked geometry.

7. The IOL according to claim 1, wherein thickness of the IOL is variable and the curvature is maintained.

8. The IOL according to claim 1, wherein thickness of the IOL is variable and the curvature is variable.

9. The IOL according to claim 1, wherein said diffractive rings comprise a repetitive pattern of a single diffractive profile.

10. The IOL according to claim 1, wherein said Fresnel zones comprise a repetitive pattern of two different diffractive profiles.

11. The IOL according to claim 1, wherein said efficiency is at least 93%.

12. The IOL according to claim 1, wherein said diffractive rings comprise a single transition from a first zone having a repetitive pattern of one diffractive profile to a second peripheral zone having a repetitive pattern of a second diffractive profile.

13. The IOL according to claim 12, wherein height of diffractive surface topography of said second peripheral zone is maintained constant when advancing radially outwards in respect to the center height of the IOL.

* * * * *